US010632280B2

(12) United States Patent
Pugh et al.

(10) Patent No.: US 10,632,280 B2
(45) Date of Patent: Apr. 28, 2020

(54) DEVICES AND METHODS FOR DELIVERING FLUID TO A NASAL CAVITY

(71) Applicant: Neosinus Health Inc, Raleigh, NC (US)

(72) Inventors: Magda R. Pugh, Raleigh, NC (US); Kashif Mazhar, Raleigh, NC (US); Michael Edward Laut, Raleigh, NC (US); Nathan McCracken, Cary, NC (US)

(73) Assignee: Neosinus Health Inc., Raleigh, NC (US)

( * ) Notice: Subject to any disclaimer, the term of this patent is extended or adjusted under 35 U.S.C. 154(b) by 26 days.

(21) Appl. No.: 15/705,773

(22) Filed: Sep. 15, 2017

(65) Prior Publication Data

US 2019/0083741 A1    Mar. 21, 2019

(51) Int. Cl.
| | | |
|---|---|---|
| *A61M 25/00* | (2006.01) | |
| *A61M 15/08* | (2006.01) | |
| *A61J 1/06* | (2006.01) | |
| *A61M 31/00* | (2006.01) | |
| *B05B 12/00* | (2018.01) | |
| *A61M 11/00* | (2006.01) | |

(52) U.S. Cl.
CPC .............. *A61M 25/007* (2013.01); *A61J 1/06* (2013.01); *A61M 11/00* (2013.01); *A61M 25/0075* (2013.01); *A61M 25/0097* (2013.01); *A61M 31/00* (2013.01); *B05B 12/00* (2013.01); *A61M 15/08* (2013.01); *A61M 2025/0006* (2013.01); *A61M 2025/006* (2013.01); *A61M 2025/0073* (2013.01); *A61M 2210/0618* (2013.01)

(58) Field of Classification Search
CPC ............ A61M 25/007; A61M 25/0075; A61M 25/0097; A61M 31/00; A61M 15/08; A61M 2025/0004; A61M 11/00; A61J 1/06; B05B 12/00
See application file for complete search history.

(56) References Cited

U.S. PATENT DOCUMENTS

| | | | | | |
|---|---|---|---|---|---|
| 4,940,061 | A | * | 7/1990 | Terwilliger | A61B 10/0275 600/567 |
| 5,249,583 | A | * | 10/1993 | Mallaby | A61B 10/0275 600/567 |
| 5,601,572 | A | * | 2/1997 | Middleman | A61B 10/02 606/139 |

(Continued)

*Primary Examiner* — Laura A Bouchelle
*Assistant Examiner* — Mark A Igel
(74) *Attorney, Agent, or Firm* — Coats & Bennett, PLLC

(57) ABSTRACT

Devices and methods for delivering fluid to the nasal cavity that include a delivery tube and cap configured to be connected to a container that houses the fluid. The delivery tube includes an inner cannula that is positioned within an outer cannula. Each of the cannulas includes a first outlet with one or more openings aligned along a first lateral section and a second outlet with one or more openings aligned along a second lateral section. The cap is configured to secure the delivery tube to the container. The delivery tube and cap are configured to provide relative axial movement between the cannulas. The cannulas are positionable between a first axial position that aligns the first outlets along the first lateral section of the delivery tube to deliver the fluid to a first portion of the nasal cavity, and a second axial position that aligns the second outlets along the second lateral section to deliver fluid to a second portion of the nasal cavity.

12 Claims, 11 Drawing Sheets

(56) References Cited

U.S. PATENT DOCUMENTS

| | | | | |
|---|---|---|---|---|
| 7,824,436 B2* | 11/2010 | Barbut | ............... | A61F 7/12 |
| | | | | 607/96 |
| 8,721,699 B2* | 5/2014 | Barbut | ............... | A61F 7/12 |
| | | | | 607/105 |
| 8,932,339 B2* | 1/2015 | Harikrishna | ............... | A61F 7/12 |
| | | | | 607/104 |
| 9,358,150 B2* | 6/2016 | Rozenberg | ............... | A61F 7/12 |
| 2002/0062119 A1* | 5/2002 | Zadno-Azizi | .... | A61B 17/12109 |
| | | | | 604/509 |
| 2004/0167473 A1* | 8/2004 | Moenning | ............ | A61B 17/3439 |
| | | | | 604/164.02 |
| 2004/0267154 A1* | 12/2004 | Sutton | ............... | A61B 10/025 |
| | | | | 600/562 |
| 2007/0213671 A1* | 9/2007 | Hiatt | ............... | A61M 25/007 |
| | | | | 604/164.01 |
| 2008/0086165 A1* | 4/2008 | Lyon | ............... | A61M 25/0017 |
| | | | | 606/191 |
| 2008/0125746 A1* | 5/2008 | Shapland | ............... | A61M 25/10 |
| | | | | 604/508 |
| 2010/0286616 A1* | 11/2010 | Baroud | ............... | A61B 17/3472 |
| | | | | 604/164.11 |
| 2012/0035501 A1* | 2/2012 | Landrigan | ............ | A61B 10/025 |
| | | | | 600/567 |
| 2013/0274711 A1* | 10/2013 | O'Day | ............... | A61M 5/16813 |
| | | | | 604/508 |
| 2014/0058353 A1* | 2/2014 | Politis | ............... | A61M 5/14248 |
| | | | | 604/506 |
| 2014/0163530 A1* | 6/2014 | Frenkel | ............... | A61M 25/003 |
| | | | | 604/540 |
| 2015/0038817 A1* | 2/2015 | Richter | ............ | G01N 33/48757 |
| | | | | 600/365 |
| 2015/0104331 A1* | 4/2015 | Dye | ............... | A61M 1/101 |
| | | | | 417/53 |
| 2015/0290421 A1* | 10/2015 | Glickman | ............ | A61M 25/007 |
| | | | | 604/31 |
| 2016/0228685 A1* | 8/2016 | Pugh | ............... | A61M 31/00 |

* cited by examiner

DEVICES AND METHODS FOR DELIVERING FLUID TO A NASAL CAVITY

TECHNICAL FIELD

The present disclosure relates to devices and methods for delivering fluid to the nasal cavity, and more particularly to expelling the fluid from specific lateral sections of the delivery device to target specific areas of the nasal cavity.

BACKGROUND

The nasal cavity comprises a variety of surfaces that correspond to anatomic structures serving various respective biological functions. Generally, the nasal cavity is divided vertically by a wall of cartilage called the septum. On each side of the septum is a nostril through which the nasal cavity can be accessed. Opposite the septum, on each lateral side of the nasal cavity, are a series of turbinates (also known as concha). Each series comprises an inferior, middle, and superior turbinate, as one goes in a posterior direction from the nostrils, through the nasal cavity, towards the throat. These turbinates are a series of bony ridges that protrude into the nasal cavity. The maxillary, anterior ethmoid, and frontal sinuses drain into the nasal cavity from under the middle turbinate, which is above the inferior turbinate.

In order to treat these anatomic structures within the nose, therapeutic fluids can be topically applied to their corresponding surfaces. Such fluids for example, include saline, antihistamines, decongestants, and corticosteroids, which may be helpful in irrigating nasal passages, treating allergies, relieving nasal congestion, and treating inflammation, respectively. To deliver these fluids to various surfaces in the nasal cavity, a spray bottle is often used. To use the spray bottle, a patient typically inserts a nozzle through their nostril and ejects fluid from the nozzle in a haphazard and indiscriminate fashion. While haphazardly and indiscriminately dispensing fluid in this fashion tends to result in at least some fluid being applied to an appropriate surface within the nasal cavity, such an approach is inefficient at best. Indeed, a large percentage of the fluid delivered by this method is often wasted by being applied to surfaces for which the fluid can deliver little to no therapeutic value.

SUMMARY

The present application is directed to devices that deliver fluid to a nasal cavity. The device may be configured to deliver the fluid predominantly and/or entirely from one lateral section. The device may be adjustable to deliver the fluid to the desired lateral section as needed for delivery fluid to the different sections of the nasal cavity. The device is further configured to be attached to a container that houses the fluid.

One embodiment is directed to a device to deliver fluid from a container to a nasal cavity. The device includes a hollow inner cannula with an inlet at a proximal end and first and second outlets positioned towards a distal end with the first and second outlets on different lateral sections. The inlet and the first and second outlets are in fluid-flow relationship. A hollow outer cannula extends over and houses the inner cannula. The outer cannula includes third and fourth outlets towards a distal end with the third and fourth outlets being on different lateral sections of the outer cannula. A cap is connected to each of the inner and outer cannulas and configured to provide relative axial movement of the inner and outer cannulas along a longitudinal axis of the cannulas between a first axial position and a second axial position. In the first axial position, the first and third outlets are aligned and the second and fourth outlets are misaligned thereby permitting the fluid to be predominantly ejected from the third outlet via the first outlet relative to the fourth outlet via the second outlet. In the second axial position, the first and third outlets are misaligned and the second and fourth outlets are aligned thereby permitting the fluid to be predominantly ejected from the fourth outlet via the second outlet relative to the third outlet via the first outlet.

The device may also include a first section that is attached to the proximal end of the inner cannula, and a second section that is rotatable relative to the first section and that includes first and second ramps that engage with the outer cannula. The first and second sections may be rotatable relative to each other in a clockwise direction to slide the outer cannula along the first ramp and move the outer cannula axially relative to the inner cannula in a first direction. The first and second sections may be rotatable relative to each other in a counter-clockwise direction to slide the outer cannula axially relative to the inner cannula in an opposing second direction.

The inner cannula may be fixedly attached to the first section of the cap to prevent movement of the inner cannula during movement of the outer cannula.

The device may include fins that extend radially outward from the outer cannula and engage with first and second ramps of the second section.

The device may include that each of the first, second, third, and fourth outlets include a plurality of openings.

The first and third outlets may include a common number of openings and the second and fourth outlets may include a common number of openings.

The device may also include an opening in the distal end of each of the inner and outer cannulas.

Another embodiment is directed to a device to deliver fluid from a container to a nasal cavity. The device includes a delivery tube with inner and outer cannulas with the inner cannula positioned within a hollow interior of the outer cannula. Each of the cannulas includes an elongated shape with a proximal end and an opposing distal end, a first outlet towards the distal end and positioned on a first lateral section, and a second outlet towards the distal end and positioned on a second lateral section. A cap is connected to each of the inner and outer cannulas and configured to axially position the inner and outer cannulas relative to one another between a first axial position and a second axial position. The first axial position includes the first outlets aligned at the first lateral section of the delivery tube and the second outlets misaligned at the second lateral section of the delivery tube to deliver the fluid in a first lateral direction. The second axial position includes the second outlets aligned at the second lateral section of the delivery tube and the first outlets misaligned at the first lateral section of the delivery tube to deliver the fluid in a second lateral direction.

The device may include that the proximal ends of each of the inner and outer cannulas may be connected to the cap.

The device may include that one of the inner cannula and the outer cannula are threaded onto a threaded portion of the cap.

The device may include that the first axial position the second outlets may overlap a lesser amount than the first outlets such that a predominant amount of the fluid is ejected from the delivery tube in the first lateral direction and a lesser amount of the fluid is ejected from the delivery tube in the second lateral direction.

The device may include that the first outlets and the second outlets of each of the inner and outer cannulas may be spaced apart around the perimeter of the cannulas by an angle of 90° or less.

The cap may include a plurality of members that each include an opening with the members being rotatably connected together and with the openings coaxially aligned.

The device may include that the inner cannula may be fixedly connected to the cap and the outer cannula may be movable relative to the cap with the inner cannula being stationary during movement of the outer cannula.

Another embodiment is directed to a method of delivering fluid from a container to a nasal cavity. The method includes: rotating a first cap member in a first rotational direction relative to a second cap member with a delivery tube with an inner cannula and an outer cannula being connected to the first and second cap members; relatively moving the outer cannula relative to the inner cannula in a first axial direction; aligning a first set of outlets on a first lateral section of the inner and outer cannulas and misaligning a second set of outlets on a second lateral side of the inner and outer cannulas with the outlets being positioned towards distal ends of the inner and outer cannulas; moving the fluid from the container into a proximal end of the inner cannula at the first and second cap members and along the inner cannula and expelling the fluid through the aligned first set of outlets on the first lateral section; rotating the first cap member in a second rotational direction relative to the second cap member; relatively moving the outer cannula relative to an inner cannula in an opposing second axial direction; aligning the second set of outlets on the second lateral section of the inner and outer cannulas and misaligning the first set of outlets on the first lateral side of the inner and outer cannulas; moving the fluid into the proximal end of the inner cannula at the first and second cap members and along the inner cannula and expelling the fluid through the aligned second set of outlets on the second lateral section.

The method may further include preventing the inner cannula from moving relative to the first and second cap members and moving the outer cannula axially along the inner cannula.

The method may further include moving the outer cannula relative to the inner cannula in the first and second axial directions and simultaneously rotating the outer cannula relative to the inner cannula.

The method may further include expelling a lesser amount of the fluid through the misaligned second set of outlets on the second lateral section of the delivery tube when expelling the fluid through the aligned first set of outlets on the first lateral side.

The method may further include moving a body of the outer cannula over the outlet on the second lateral section of the inner cannula and preventing the fluid from being expelled on the second lateral section when the fluid is being expelled on the first lateral side through the aligned first second of outlets.

The various aspects of the various embodiments may be used alone or in any combination, as is desired.

DETAILED DESCRIPTION

Figure 1:
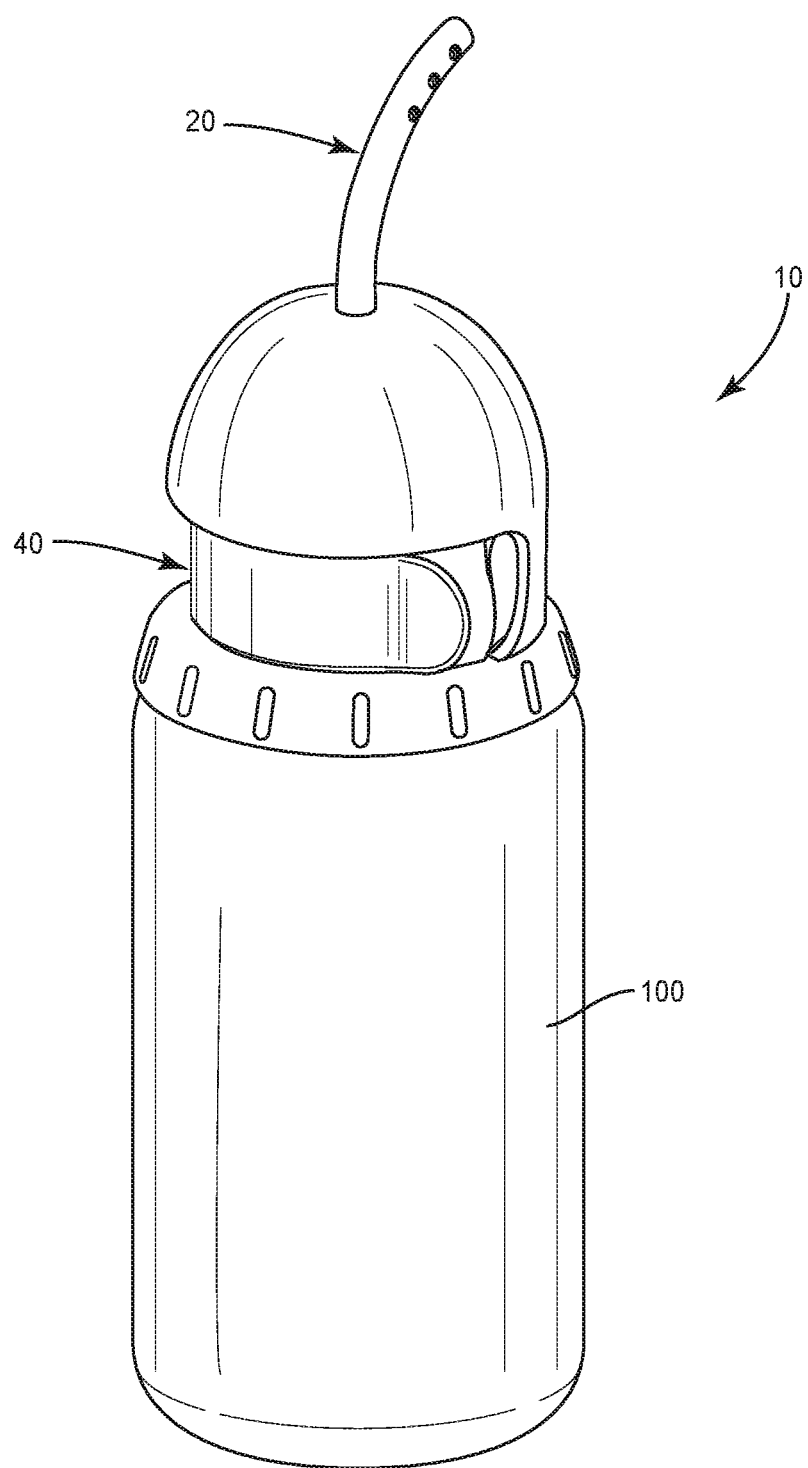
FIG. 1 is a perspective view of a delivery device connected to a container.

The present application is directed to devices and methods for delivering fluid from a container to the nasal cavity. One device includes a delivery tube and cap configured to be connected to a container that houses the fluid. The delivery tube includes an inner cannula that is positioned within an outer cannula. Each of the cannulas includes a first outlet with one or more openings aligned along a first lateral section and a second outlet with one or more openings aligned along a second lateral section. The cap is configured to secure the delivery tube to the container. The delivery tube and cap are configured to provide relative axial movement between the cannulas. The cannulas are positionable between a first axial position that aligns the first outlets along the first lateral section of the delivery tube to deliver the fluid to a first portion of the nasal cavity, and a second axial position that aligns the second outlets along the second lateral section to deliver fluid to a second portion of the nasal cavity.

The fluids that are delivered in accordance with aspects of the present disclosure may be made by dissolving a tablet in a predetermined amount of distilled water. According to one aspect of the present disclosure, a tablet is provided for ease of use as opposed to powder form, which has been determined to be both cumbersome and otherwise overly reliant on the expertise of a particular user/consumer. Such tablets are contemplated as being provided to a user in the form of a solution preparation kit. In one alternate aspect, a solution may be included in a kit, however, the tablet form may increase ease, precision, and extend the shelf life of the kit, according to particular embodiments.

Examples of preparation for the tablets as may be included in the kit are provided below. The tablets may further comprise amounts of buffers, dissolving agents, complexing agents, and the like that would not interfere with the desired and predetermined parameters stated in Table 1 below. In other words, the tablets may comprise additional non-listed compounds that would not affect desired predetermined pH values, dissolving time, overall tablet weight, and/or other desirable factors.

In a particular example, a tablet was made for use in preparing a solution/rinse for irrigating a nasal cavity according to an aspect of the present disclosure. An amount of sodium chloride (120 mg); sodium bicarbonate (290 mg); and citric acid (40 mg) was combined with the use of a mortar and pestle. The resulting mixture was molded into a 450 mg tablet via use of a hydraulic press (Kahan Analytical Solutions, Dehli, India). The press applied a pressure equal to 7 tons/m² at a temperature of 25° C. The tablet was then dried for at least five seconds at a temperature of 25° C.

A solution was prepared using the tablet made as described above. The tablet was dissolved in 100 ml of distilled water having a temperature of 40° C. (104° F.). The tablet dissolved substantially completely within about 30 sec. The resulting solution (after tablet dissolution) had a pH of about 6.98. A non-exhaustive listing of other useful tablet compositions made and tested for tableting compounds for use in preparing solutions used according to aspects of the present disclosure are provided below in Table 1.

TABLE 1

| Capsule | Sodium Chloride (mg) | Sodium bicarbonate (mg) | Citric Acid (mg) | Tablet wt. (mg) | pH | Dissolution time (sec) | Dissolution Vol. (ml) |
|---|---|---|---|---|---|---|---|
| NaCl | 120 | 290 | 40 | 450 | 6.98 | 20 | 132 |
| Mupirocin | 120 | 290 | 40 | 465 | 6.71 | 21 | 132 |
| Budesonide + mupirocin (15.6 mg) | 120 | 290 | 40 | 465.5 | 6.42 | 10 | 132 |
| Budesonide (0.6 mg) | 120 | 290 | 40 | 450.6 | 6.21 | 31 | 132 |

The fluid is delivered to the nasal cavity by a delivery device 10. For example, FIG. 1 illustrates a device 10 connected to a container 100. The device 10 includes a delivery tube 20 sized to be inserted into the user's nasal cavity. The device 10 also includes a cap 40 that connects the delivery tube 20 to the container 100. The cap 40 is movable to adjust the delivery tube 20 to selectively deliver the fluid in the container 100 to selected portions of the nasal cavity.

Figure 2:
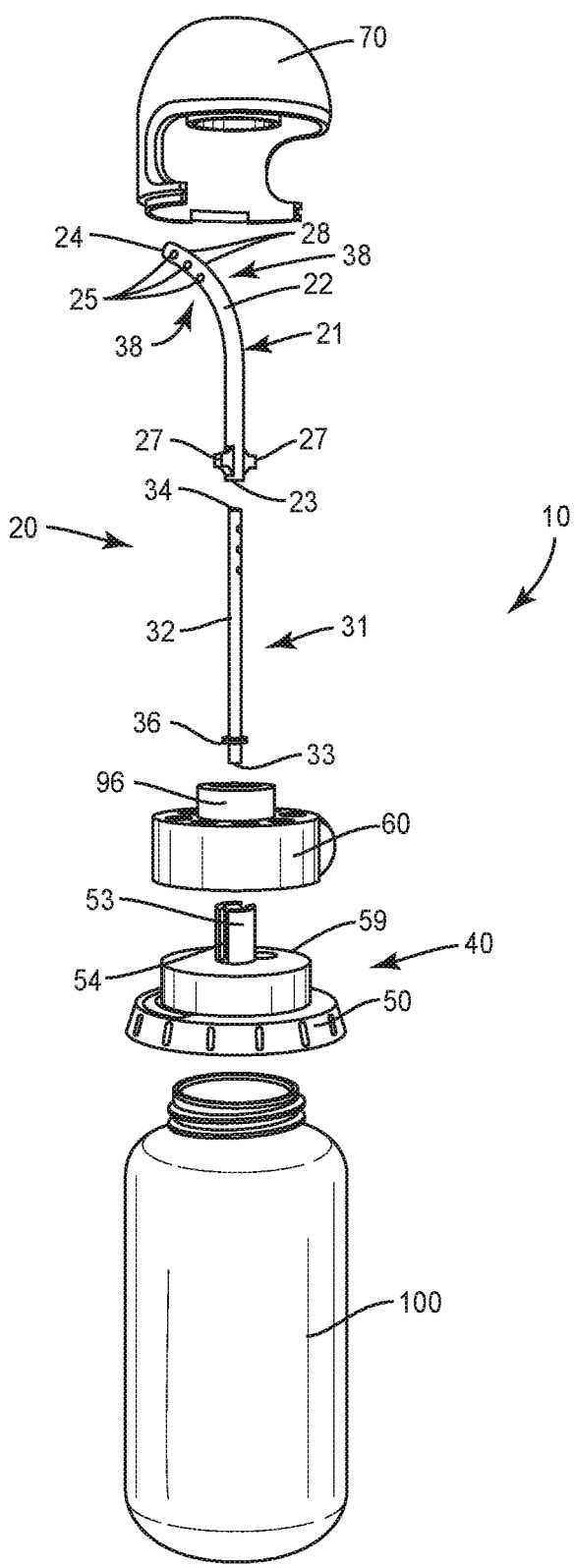
FIG. 2 is an exploded perspective view of a delivery device and a container.

FIG. 2 illustrates an exploded view of a device 10 and a container 100. The delivery tube 20 is constructed from an outer cannula 21 and an inner cannula 31. The cannulas 21, 31 are configured to move axially relative to one another to provide for selective delivery of the fluid into the nasal cavity. The cap 40 is constructed from a base cap 50, an intermediate cap 60, and a top cap 70. The cap 40 is configured to be removably attached to the container 100.

Figure 3:
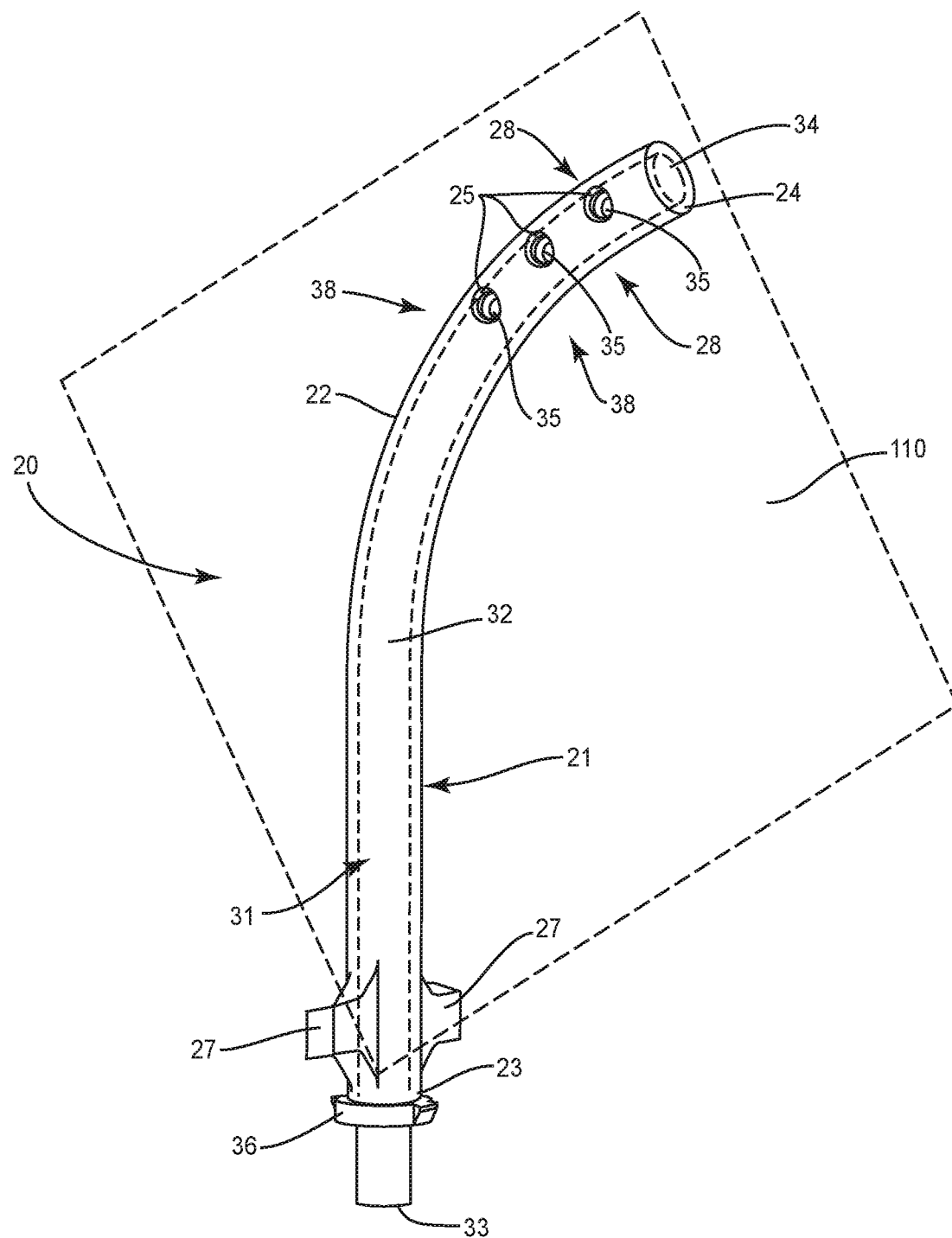
FIG. 3 is a perspective view of a delivery tube with an outer cannula extending over and housing an inner cannula.

FIG. 3 illustrates the delivery tube 20 with the inner cannula 31 positioned within the outer cannula 21. The delivery tube 20 may include a curving centerline along a geometric plane 110 that for purposes of explanation divides the delivery tube 20 into first and second lateral sections. The delivery tube 20 may also include other shapes as necessary to deliver the fluid to the nasal cavity, including but not limited to a straight shape. The lateral sections of the delivery tube 20 may be separated by different amounts of angular separation around the delivery tube 20. One design includes the lateral sections being on opposing sides of the delivery tube 20 (i.e., 180° apart). Other designs feature a small angular separation that is 90° or less. Other designs feature between 90°-180°.

The delivery tube 20 and the cap 40 may be constructed from various materials, including but not limited to plastics and rubber. The cannulas 21, 31 may be flexible to facilitate insertion into the nasal cavity and prevent possible injury to the user with the cap 40 being constructed from more rigid materials. The cannulas 21, 31 may be constructed from the same or different materials. FIG. 2 includes an embodiment with the outer cannula 21 constructed from a stiffer material than the inner cannula 31. The stiffer construction provides for the outer cannula 21 to have a curved shape. The more flexible inner cannula 31 assumes this shape when inserted into the outer cannula 21.

As illustrated in FIGS. 2 and 3, the outer cannula 21 includes an elongated body 22 with a proximal end 23 and an opposing distal end 24. The proximal end 23 is open and leads into a hollow interior that extends the length of the body 22. One or more fins 27 are positioned towards the proximal end 23. One design includes two fins 27 that extend radially outward on opposing sides of the body 22. Other designs include a different number of fins 27 and/or different angular arrangements.

Outlets 28 are positioned towards the distal end 24 of the body 22. The outlets 28 are positioned on different lateral sections of the body 22 to dispel the liquid in different lateral directions. Each outlet 28 includes one or more openings 25. The openings 25 of each outlet 28 may be aligned in a longitudinal column along the body 22. Other designs include the openings 25 being offset at different angular orientations along the body 22. The different outlets 28 may include the same or different number of openings 25, and the openings 25 may have the same or different shapes and/or sizes.

The distal end 24 of the outer cannula 21 may be closed to prevent the ejection of fluid. Another design includes the distal end 24 having an opening to dispel fluid outwardly and into the nasal cavity.

The inner cannula 31 is sized to fit within the hollow interior of the outer cannula 21. The inner cannula 31 includes an elongated body 32 with a proximal end 33 and an opposing distal end 34. The proximal end 33 is open and leads into a hollow interior that extends the length of the body 32. The distal end 34 may be closed or open depending upon whether fluid is to be ejected outward in the distal direction. The inner cannula 31 also includes a flange 36 in proximity to the proximal end 33. The flange 36 has a larger diameter than the remainder of the body 32 and provides for securing the inner cannula 31 in the cap 40.

Outlets 38 each with one or more openings 35 are positioned on different lateral sections of the body 32 in proximity to the distal end 34. The openings 35 in the outlets 38 may be aligned in a longitudinal column, or may have an angular offset between openings 35. The outlets 38 may have the same or a different number of openings 35 and may have the same or different shapes and/or sizes. In one design, each of the inner and outer cannulas 21, 31 includes two outlets 28, 38. Other designs may include a single outlet 28, 38 on one or both cannulas 21, 31, or three or more outlets 28, 38 on one or both cannulas 21, 31.

The outer cannula 21 includes a larger sectional size than the inner cannula 31. This provides for relative axial movement between the cannulas 21, 31. In one design, the cannulas 21, 31 include the same sectional shape with one specific design including each having a circular section shape. Other designs may include different sectional shapes, provided the sizing allows for relative axial movement between the cannulas 21, 31. In one design, the relative axial movement occurs by the outer cannula 21 moving relative to the stationary inner cannula 31. Other designs include an axially movable inner cannula 31 and stationary outer cannula 21, and movable inner and outer cannulas 21, 31.

Figure 4:
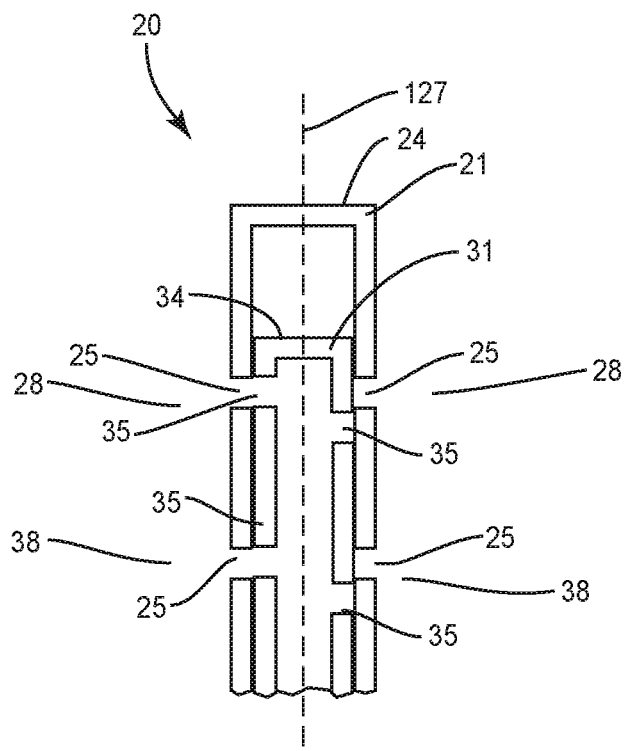
FIG. 4 is a schematic section view of the outer cannula at an axial position relative to an inner cannula to deliver fluid in a first lateral direction.

The cannulas 21, 31 are configured to axially move relative to each other to position the outlets 28, 38 to control the direction that fluid is expelled from the delivery tube 20. FIG. 4 illustrates the cannulas 21, 31 at a relative axial position with the inner cannula 31 positioned within the hollow interior of the outer cannula 21. In this axial position, the inner cannula 31 is positioned within the outer cannula 21 such that the openings 25 of one of the outlets 28 of the outer cannula 21 is aligned with the openings 35 of one of the outlets 38 of the inner cannula 31 along one lateral section of the delivery tube 20. As viewed in FIG. 4, the openings 25, 35 are aligned along the left of the delivery tube 20. This provides for fluid that is moved through the delivery tube 20 to be expelled in this lateral direction. The openings 35 of the outlet 38 of the inner cannula 31 on the opposing lateral section are aligned with the body 22 of the outer cannula 21. This blocks the openings 35 of the outlet 38 thus preventing fluid from being expelled from the delivery tube 20 in this lateral direction.

In one design, the openings 35 of the outlet 38 may be partially aligned with the openings 25 of the outlet 28 on this opposing lateral section. This provides for some of the fluid to be ejected in this second lateral direction, although substantially more fluid is ejected through the aligned outlets 28, 38 on the first lateral section.

Figure 5:
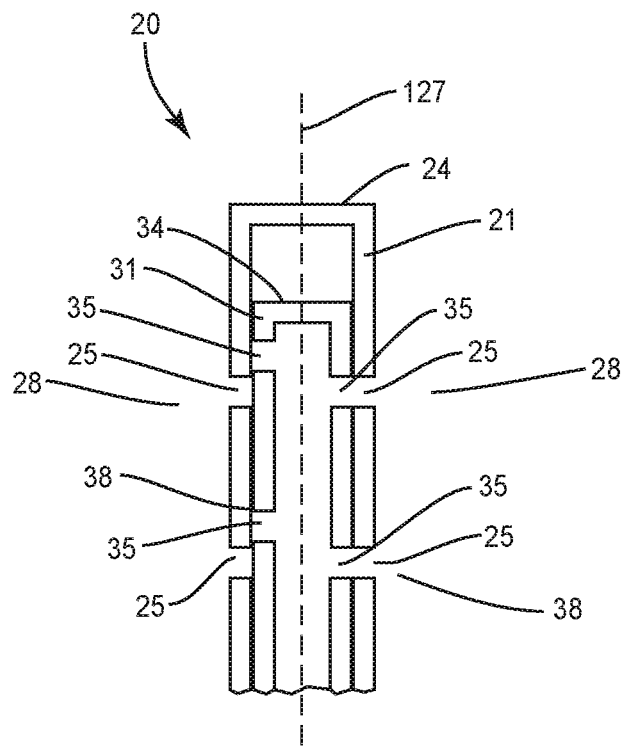
FIG. 5 is a schematic section view of the outer cannula at an axial position relative to an inner cannula to deliver fluid in a second lateral direction.

FIG. 5 illustrates an axial position in which the inner and outer cannulas 21, 31 have axially moved relative to one another. This movement locates the openings 35 of outlet 38 along the opposing lateral section of the inner cannula 31 with the corresponding openings 25 of outlet 28 of the outer cannula 21. This provides for expelling the fluid in this lateral direction. This axial position further blocks the fluid from being expelled in the opposing lateral direction as the openings 35 of the outlet 38 are aligned with the body 22 of the outer cannula 21. Also, the design may also provide for a smaller amount of fluid to be expelled from this blocked lateral section as the outlets 28, 38 may have some overlap.

FIGS. 4 and 5 include designs in which fluid can be expelled completely or predominantly from just one lateral sections of the delivery tube 20. The cannulas 20, 30 may be configured with the openings 25, 35 sized and/or positioned to provide for expelling different amounts of fluid on the different lateral sections. By way of example, in a particular relative axial position, the size of the overlapped openings 25, 35 of the outlets 28, 38 on a first lateral section may be a first amount to provide for a first amount of fluid to be expelled, and the overlapping openings 25, 35 on the second lateral section is smaller or larger such that a different amount of fluid is expelled. This design provides for the user and/or manufacturer to control the amount and direction of fluid as necessary.

The delivery tube 20 may also be positioned in a closed position in which the outlets 25, 35 are not aligned along either lateral section. This may be used for storage or when the device 10 is not in use.

The cannulas 21, 31 are connected to the cap 40 to provide for the user to adjust the relative axial positioning as necessary. The cap 40 may be configured to prevent movement of one of the cannulas 21, 31, and provide for movement of the other cannula 21, 31 for the different axial positions. The cap 40 may also be configured to allow movement of each of the cannulas 21, 31 to provide for the positioning. In one design, the cap 40 maintains the inner cannula 31 stationary and provides for axial movement of just the outer cannula 21.

The cap 40 includes multiple members that are movable relative to one another. Relative movement of the cap members in a first direction provides for moving one of the cannulas 21, 31 relative to the other in a first axial direction. Relative movement of the cap members in a second direction provides relative axial movement of the cannulas 21, 31 in a second direction.

In one design, the cap 40 comprises three members that provide for the relative movement. This includes a base cap 50, an intermediate cap 60, and a top cap 70.

Figure 6:
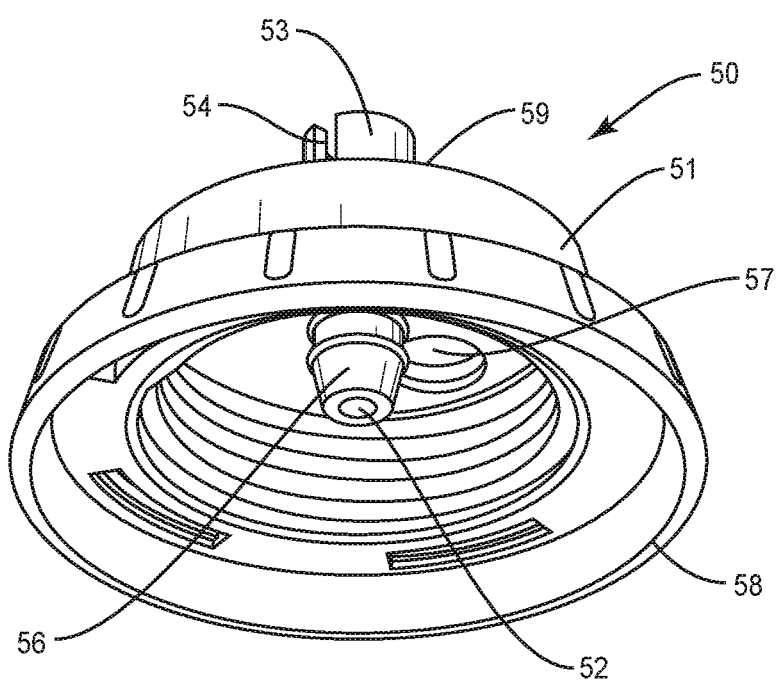
FIG. 6 is a perspective view of a lower portion of a base cap.

FIG. 6 illustrates a bottom side of the base cap 50 that attaches to the container 100 (FIG. 2 illustrates a top side of the base cap 50). The base cap 50 includes a concave body 51 with an open bottom 58 and a closed top 59. An opening 52 extends through the body 51 from the bottom 58 to the top 59. The interior of the body 51 at the bottom 58 includes threads to engage with corresponding threads on the container 100 to secure the base cap 50. The body 51 is configured to mount a tube (not illustrated) at the bottom 58 such that the tube is aligned with the opening 52 and extends into the interior of the container 100. A fitting 56 extends around the opening 52 and may include a conical shape with one or more flanges configured to fit within an end of the tube. The top 59 of the base cap 50 includes a neck 53 that extends outward from the body 51 at the opening 52. A slot 54 may be cut across the neck 53. An opening 57 extends through the base cap 50. The opening 57 may be positioned in proximity to the opening 52 as illustrated in FIG. 6.

The inner cannula 31 mates with the base cap 50. In one design, the inner cannula 31 is inserted from the bottom 58 through the opening 52 of the base cap 50. The opening 52 is sized such that the flange 36 towards the proximal end 33 of the inner cannula 31 engages with fitting 56 and prevents the cannula 31 from being completely pulled through the base cap 50. Another design includes the base cap 50 having a receptacle at the opening 52 to receive and secure the proximal end 33 of the inner cannula 31 via a press-fit engagement.

Figure 7:
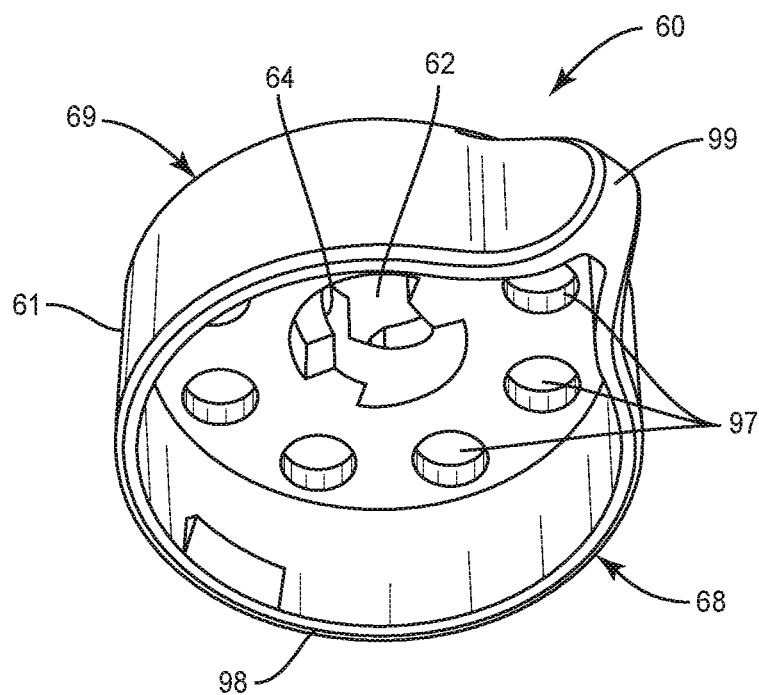
FIG. 7 is a perspective view of a lower portion of an intermediate cap.
Figure 8:
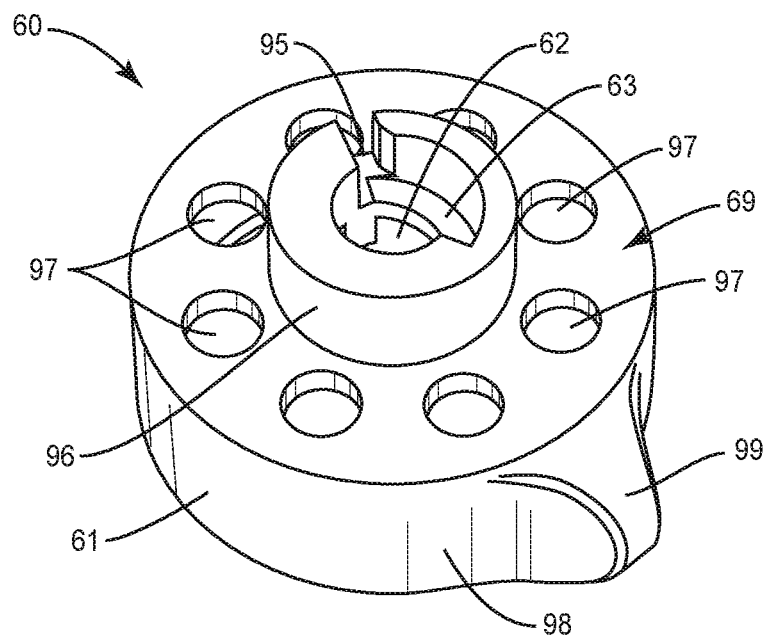
FIG. 8 is a perspective view of an upper portion of an intermediate cap.

The intermediate cap 60 is positioned over the base cap 50. FIG. 7 illustrates a bottom view of the intermediate cap 60 and FIG. 8 illustrates a top view. The intermediate cap 60 includes a body 61 with a concave shape with an open bottom 68 and a closed top 69. The body 61 includes an outer wall 98 that extends around and forms a cavity sized to receive the base cap 50. A handle 99 is formed by the outer wall 98 to rotate the intermediate cap 60 as will be explained below. An opening 62 extends through a central point of the body 61 from the bottom 68 to the top 69. The opening 62 is sized to receive the neck 53 of the base cap 50. The body 61 also includes a neck 96 that extends upward from a top of the cap 60. The cap 60 also includes additional openings 97 in the body 61 that are positioned in proximity to the central opening 62.

Ramps 63, 64 are positioned along the inner side of the neck 96 at the opening 62. The first ramp 63 extends around a portion of the first side of the opening 62, and the second ramp 64 extends around a portion on the opposing second side of the opening 62. Each of the ramps 63, 64 includes a contact surface that contact with one of the fins 27 on the outer cannula 21. One of the ramps 63, 64 is positioned to contact against a bottom edge of one of the fins 27. The opposing ramp 63, 64 is positioned to contact against a top edge of the opposing fin 27. Further, the first ramp 63 is angled in a first direction to push the contacted fin 27 either up or down during rotation of the intermediate cap 60. The second ramp 64 is angled in an opposite direction to push the contacted fin in the opposite direction during rotation of the cap 60. In one embodiment, ramp 63 is angled to push the fin 27 upward when the intermediate cap 60 is rotated clockwise and the second ramp 64 is configured to push the contacted fin 27 downward when the intermediate cap 60 is rotated counterclockwise.

As illustrated in FIG. 8, the neck 96 of the intermediate cap 60 includes a slot 95 that is in communication with the central opening 62. The slot 95 provides for insertion of the fins 27 of the outer cannula 21 during assembly.

Figure 9:
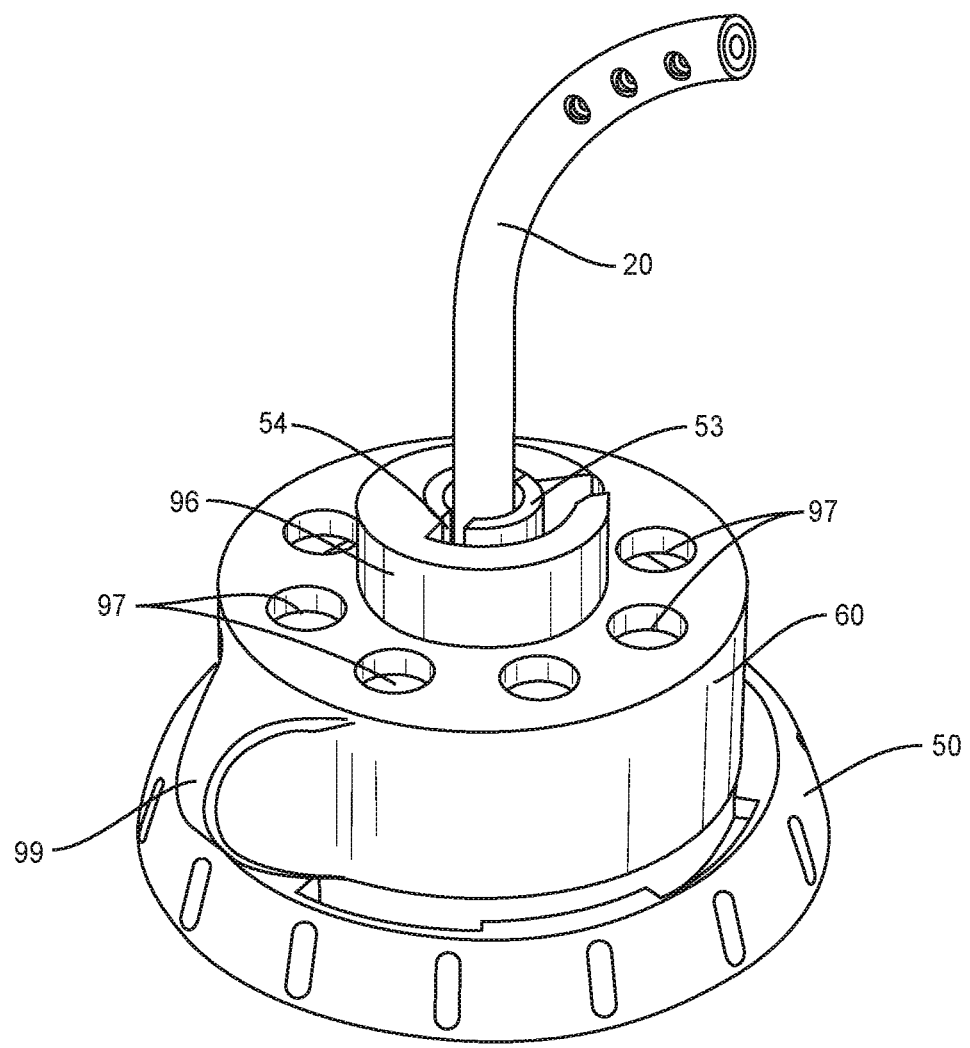
FIG. 9 is a perspective view of a base cap and an intermediate cap assembled together and a delivery tube extending outward therefrom.

FIG. 9 illustrates the base cap 50 and the intermediate cap 60 fitted together. The caps 50, 60 are connected together to provide for relative rotation between the two members. The neck 53 of the base cap 50 extends through the opening 62 of the intermediate cap 60 and is positioned within the neck 96 of the intermediate cap 60. The fins 27 (not illustrated) of the outer cannula 21 are positioned at the ramps 63, 64 (not illustrated). The delivery tube 20 extends outward from the caps 50, 60 and is aligned with the openings 52, 62.

The openings 97 of the intermediate cap 60 are positioned above the top of the base cap 50. During relative rotation between the intermediate cap 60 and the base cap 50, one of the openings 97 aligns with the opening 57 in the base cap 50. This provides for air flow into the container 100 after the fluid is expelled through the delivery tube 20. This prevents an air lock from occurring which could prevent or limit the amount of fluid that is delivered through the delivery tube 20 and/or increase the amount of time necessary between fluid expulsion procedures.

Figure 10:
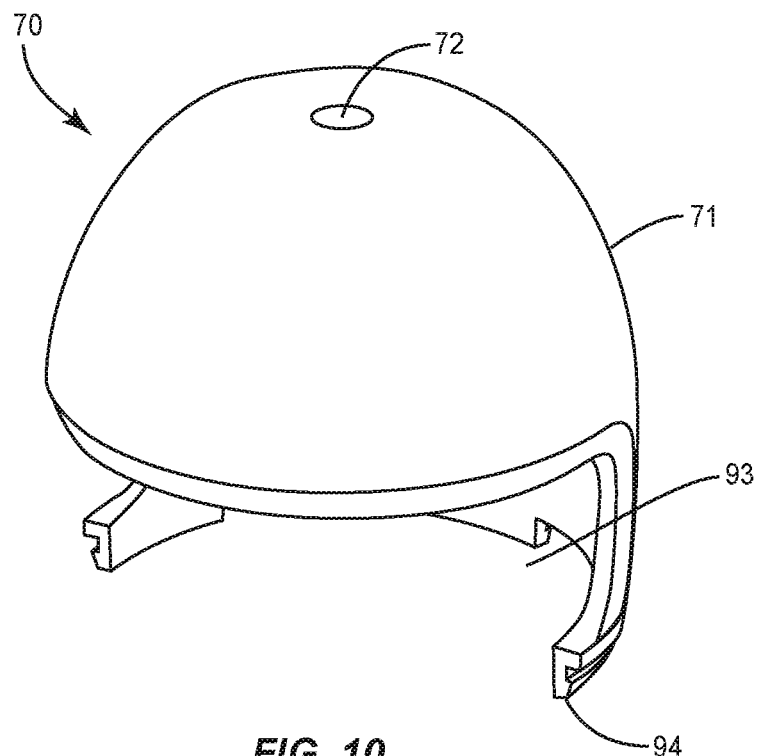
FIG. 10 is a perspective view of an upper portion of a top cap.
Figure 11:
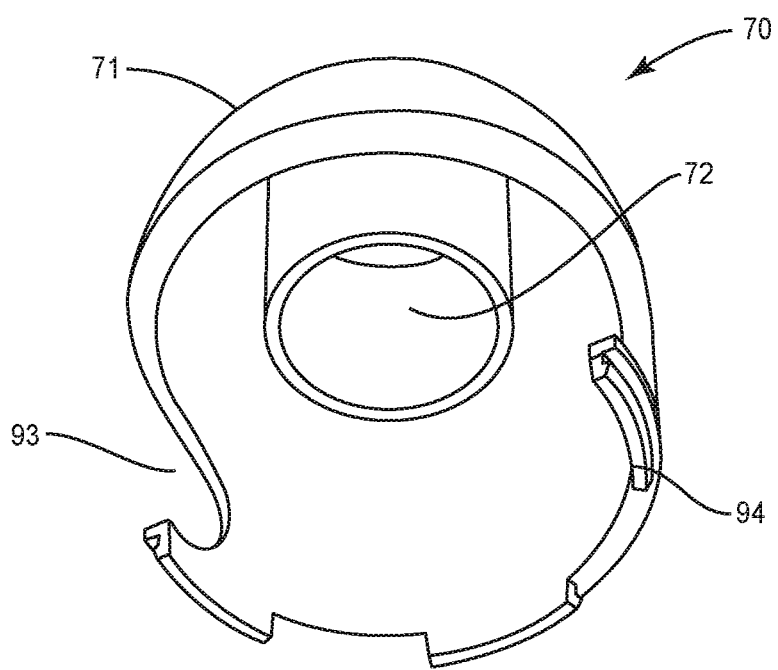
FIG. 11 is a perspective view of a lower portion of a top cap.

The top cap 70 as illustrated in FIGS. 10 and 11 is sized to extend over the intermediate cap 60. The top cap 70 includes a concave body 71 with a central opening 72 sized to receive the delivery tube 20. A bottom edge 94 of the body 71 is sized to engage with the intermediate cap 60 and/or the base cap 50. A window 93 is positioned at the bottom edge 94 along one portion of the body 71 to receive the handle 99 as will be explained below.

Assembly of the cap 40 may initially include attaching the delivery tube 20 to the base cap 50. In one design, the inner cannula 31 is inserted through the opening 52 from the bottom side of the cap 50. The inner cannula 31 is inserted through the opening 52 until the ridge 36 abuts against the fitting 56 that extends downward from the base cap 50 at the opening 52. In this position, the cannula 31 extends through the base cap 50 and the distal end 34 is spaced upward above the base cap 50.

Once positioned, a tube may be attached to the fitting 56 on the bottom of the base cap 50 at the opening 52. The tube may extend over ridges on the fitting 56 and extend downward from the base cap 50 to be positioned within the interior of the container 100 when the device 10 is attached to the container 100.

The base cap 50 and inner cannula 31 is then attached to the intermediate cap 60. This includes inserting the inner cannula 31 through the central opening 62 from the bottom of the cap 60. Insertion positions the neck 53 of the base cap 50 into the neck 96 of the intermediate cap 60. In one design, one of the slots 54 on the neck 53 of the base cap 50 is aligned with the slot 95 on the intermediate cap 60. The base cap 50 positioning also locates the bottom edge of the body 61 of the intermediate cap 60 against or in proximity to the top edge of the intermediate cap 60.

The outer cannula 21 may then be inserted over the inner cannula 31. This insertion includes aligning the proximal end 23 of the outer cannula 21 with the distal end 34 of the inner cannula 31 and then sliding the outer cannula 21 over and along the length of the inner cannula 31. The fins 27 on the outer cannula 21 slide into the slots 54 on the neck 53 of the base cap 50. The outer cannula 21 may be inserted until the fins 27 abut against a bottom of the slots 54. This also locates the fins 27 at the ramps 63, 64 in the intermediate cap 60.

The top cap 70 is then connected by aligning the distal tip of the delivery tube 20 with the opening 72. The top cap 70 is then moved relative to the delivery tube 20 and into contact with the base cap 50. In one design, the bottom edge 94 of the top cap 70 seats within a groove that extends along the outer perimeter of the base cap 50. The top cap 70 is positioned with handle 99 on the intermediate cap 60 extending through the window 93.

Once assembled, the cap 40 can be attached to the container 100. The base cap 50 includes threads that mate with threads on the neck of the container 100. This positions the tube that is attached to the bottom of the base cap 50 into the interior of the container 100. This also positions the delivery tube 20 extending outward from the cap 40.

Figure 12:
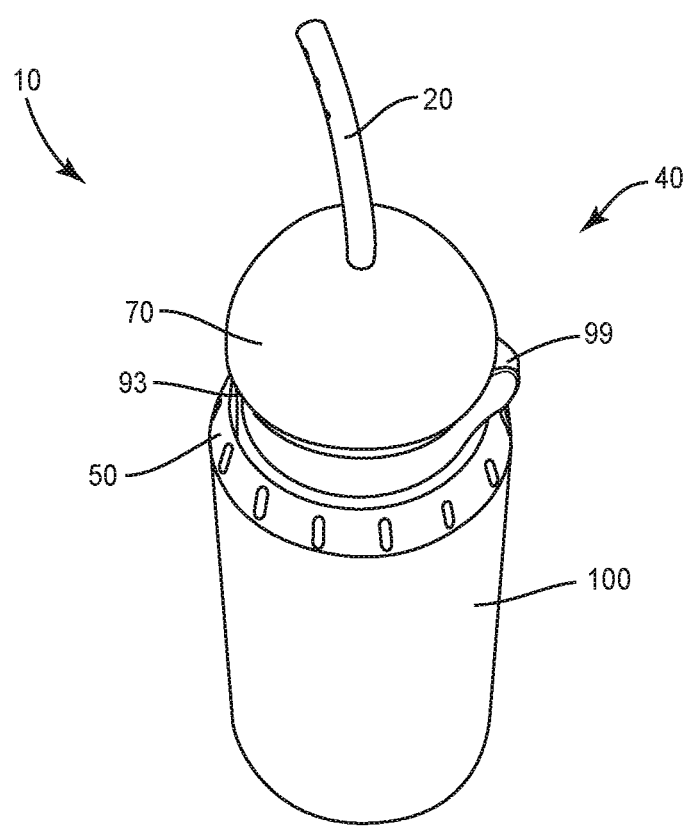
FIG. 12 is a perspective view of a delivery device in a first position and attached to a container.
Figure 13:
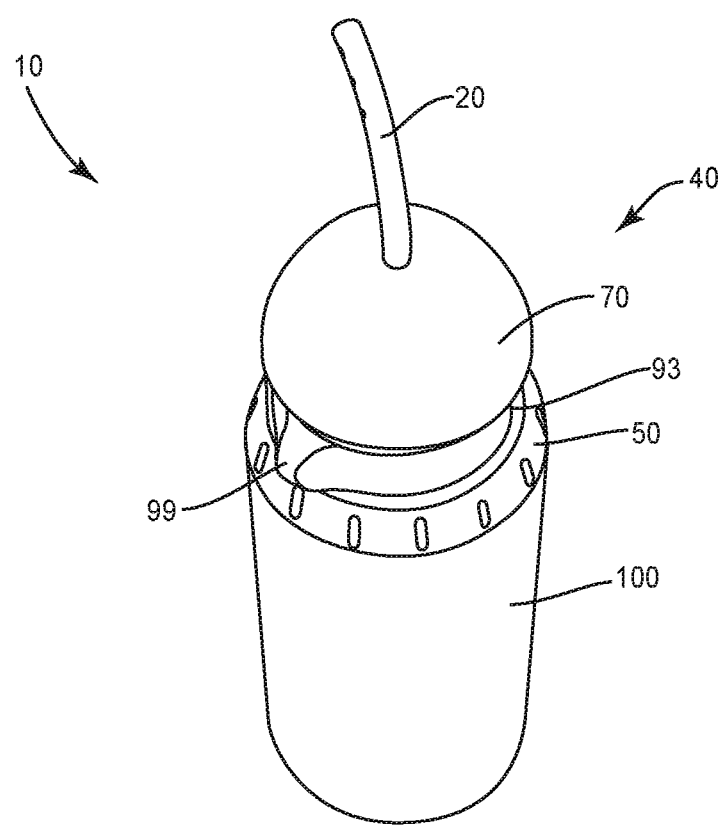
FIG. 13 is a perspective view of a delivery device in a second position and attached to a container.

FIGS. 12 and 13 illustrate the assembled cap 40 attached to the container 100. The cap 40 is in a first position in FIG. 12 with the handle 99 positioned at a first end of the window 93. This position includes the inner cannula 31 at a first axial position relative to the outer cannula 21. FIG. 13 illustrates a second position with the intermediate cap 60 rotated to a different position with the handle 99 at an opposing second end of the window 93. This positions the inner cannula 31 at a different axial position relative to the outer cannula 21.

Rotation of the intermediate cap 60 relative to the remainder of the cap 40 is accomplished by the user grasping and moving the handle 99 to the different rotational positions. Rotation in a first direction causes one of the fins 27 on the outer cannula 21 to slide along one of the ramps 63, 64 on the intermediate cap 60. This sliding movement along the ramp causes relative axial movement with the inner cannula 31. During the sliding movement, the outer cannula 21 is prevented from rotating with the intermediate cap 60 because the fins 27 are positioned in the slots 54 in the neck of the base cap 50. In one specific embodiment, rotation of the intermediate cap 60 in a clockwise rotational direction causes a bottom edge of a first fin 27 to slide along a first ramp 63 and move the outer cannula 21 distally relative to the inner cannula 31. Rotation of the intermediate cap 60 in a counter-clockwise rotational direction causes a top edge of a second fin 27 to slide along a second ramp 64 and move the outer cannula 21 proximally relative to the inner cannula 31.

The extent of rotation of the intermediate cap 60 controls the extent of relative axial movement between the cannulas 21, 31. In one design, positioning of handle 99 at the first end of the window 93 aligns the outlets 28, 38 along a first lateral side of the delivery tube 20. Positioning the handle 99 at the second end of the window 93 aligns the outlets 28, 38 along an opposing second lateral side of the delivery tube. The extent of alignment of the outlets 28, 38 can be controlled by the user based on the positioning of handle 99 within the window 93. In one design, positioning the handle 99 at a midpoint along the window 93 causes the outlets 28, 38 to be misaligned and for the cap 40 to be in a closed position to prevent fluid from being expelled. The cap 40 is configured for the user to feel the contact between the handle 99 and the ends of the window 93 to know that the desired position has been obtained for delivery of the fluid. Further, the user is able to visually see the positions.

Delivery of the fluid from the container 100 through the delivery tube 20 is accomplished by the user squeezing the container 100. This delivery forces the fluid from the container into the tube connected to the bottom of the base cap 50 and into and through the delivery tube 20. The fluid is then expelled through the outlets 28, 38 that are aligned. Releasing the container 100 causes the container to move back to its original shape. Air is drawn into the interior of the container through the opening 57 in the base cap 50 that is aligned with one or more of the openings 97 of the intermediate cap 60.

The cap 40 may also include other designs that provide relative axial movement between the cannulas 21, 31. One design includes the outer cannula 21 being axially movable and rotatable relative to the inner cannula 31. Specifically, the outer cannula 21 is threaded onto the neck 53 of the base cap 50. The outer cannula 21 includes threads 26 that extend along the inner surface of the distal end 24 that mate with threads that extend along the neck 53. Further, the fins 27 of the outer cannula 21 are engaged with receptacles 65 in the intermediate cap 60. With the fins 27 engaged in the receptacles, rotation of the intermediate cap 60 in a first direction causes the outer cannula 21 to rotate around the neck 53 in a first direction. The threads engage together and cause the outer cannula 21 to rotate about the neck 53 and also move axially relative to the inner cannula 31 in a first direction. The axial movement results in the outlets 28, 38 being aligned and misaligned as necessary. Likewise, rotation of the intermediate cap 60 in the opposing second direction causes the outer cannula 21 to rotate about the neck 53 in the second direction. This causes the outer cannula 21 to both rotate around the inner cannula 31 and move axially relative to the inner cannula 31. The amount of axial movement and rotation of the outer cannula 21 relative to the inner cannula 31 may vary.

Figure 14A:
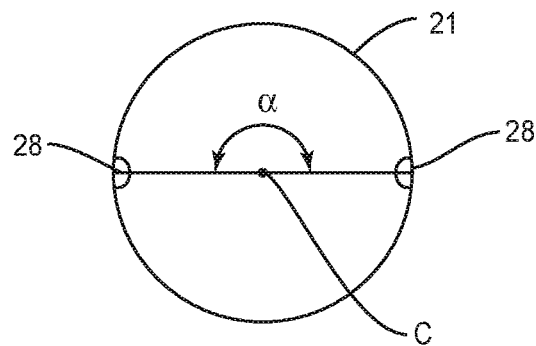
FIG. 14A is a schematic view of angular orientations between first and second outlets of an outer cannula.
Figure 14B:
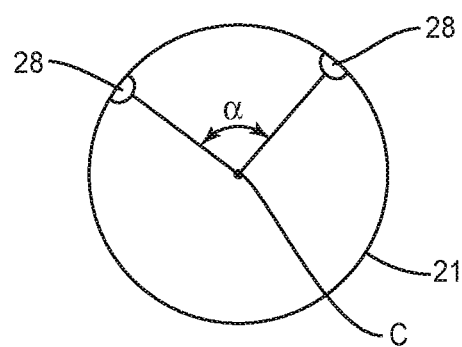
FIG. 14B is a schematic view of angular orientations between first and second outlets of an outer cannula.

The outlets 28 may be separated by different angular placements around the outer cannula 21. FIG. 14A illustrates a schematic end view of the outlets 28 aligned at different lateral sections around the outer cannula 21. The outlets 28 that each includes one or more openings 25 are separated by an angle α. FIG. 14A includes an angular placement α of about 180° between the outlets 28. FIG. 14B includes an angular placement α of about 90°. Other designs may include different angular orientations, including a range of 90° and less, and between 90°-180°.

The angular orientations α between the outlets 38 of the inner cannula 31 may be the same or different than those of the outlets 28 of the inner cannula 21. In one design, each of the inner and outer cannulas 21, 31 includes two outlets 28, 38. Other designs may include a single outlet 28, 38 on one or both cannulas 21, 31, or three or more outlets 28, 38 on one or both cannulas 21, 31.

Another design for relative axial movement between the cannulas 21, 31 includes the user applying a force and moving the outer cannula 21 along the inner cannula 31. The cannulas 21, 31 may include stops that control the extent of relative axial movement. In one design, the inner cannula 31 includes a radial extension that fits within a slot in the outer cannula 21. The extension contacts against upper and lower edges of the slot to control the extent of axial movement. In another design, the outer cannula 21 is fixed to the cap 40 and the inner cannula 31 is axially movable. A radial extension extends outward from the inner cannula 31 and extends through a slot in the outer cannula 21. The user grasps the extension to apply forces to move the inner cannula 31 upward and downward within the outer cannula 21.

Another design includes each of the intermediate and top caps 60, 70 having ramped surfaces. The outer cannula 21 is located such that the fins 27 are positioned between the ramped surfaces. This maintains the outer cannula 21 attached to the cap 40. A biasing member, such as a spring or piece of cushion material, biases the fins 27 against one of the ramped surfaces. Rotation of the intermediate cap 60 in a first direction causes the fins 27 to slide along one of the ramped surfaces and move the outer cannula 21 axially along the inner cannula 31 in a first direction. Rotation of the intermediate cap 60 in the opposing second direction causes the fins 27 to slide along the other ramped surface and move the cannula 21 axially in a second direction. In this manner, the user is able to align the outlets 28, 38 as necessary to direct the fluid.

A delivery device for delivering fluid to the nasal cavity that includes cannulas is disclosed in U.S. Patent Publication No. 2016/0228685 which is hereby incorporated by reference in its entirety.

The embodiments describe the device 10 being attached to a container 100, such as a bottle. The device 10 may also be attached to various other types of containers 100. Examples include but are not limited to a hose and a bag. The various containers 100 may be deformable by the user to force the fluid into the device 10, or may be non-deformable and require delivery to the device 10 in other manners such as gravity with the user tipping the container 100 to move the fluid into the device 10, and a pump that delivers the fluid from the container to the device 10.

A tube may be connected to the device 10 and extend into the container 100. Fluid from the container 100 enters into the tube and then enters the device 10 for delivery to the patient. Other designs do not include a tube, but rather the fluid enters directly from the container 100 into the device 10.

The various devices 10 may be used during surgical procedures on living patients. These may also be used in a non-living situation, such as within a cadaver, model, and the like. The non-living situation may be for one or more of testing, training, and demonstration purposes.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc. and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive.

What is claimed is:

1. A device to deliver fluid from a container to a nasal cavity, the device comprising:
   a hollow inner cannula comprising an inlet at a proximal end of the inner cannula and first and second outlets positioned towards a distal end of the inner cannula with the first and second outlets on different lateral sections, the inlet and the first and second outlets being in fluid-flow relationship;
   a hollow outer cannula that extends over and houses the inner cannula, the outer cannula comprising third and fourth outlets exposed to an exterior of the device and towards a distal end of the outer cannula, the third and fourth outlets on different lateral sections of the outer cannula; and
   a cap connected to both the inner cannula and the outer cannula and configured to provide relative axial movement of the inner and outer cannulas along a longitudinal axis of the cannulas between a first axial position and a second axial position;
   wherein the cap comprises a first section that is attached to the proximal end of the inner cannula, and a second section that is rotatable relative to the first section and that includes first and second ramps that engage with the outer cannula;
   wherein the first and second sections are rotatable relative to each other in a clockwise direction to slide the outer cannula along the first ramp and move the outer cannula axially relative to the inner cannula in a first direction;
   wherein the first and second sections are rotatable relative to each other in a counter-clockwise direction to slide the outer cannula axially relative to the inner cannula in an opposing second direction;
   wherein, in the first axial position, the first and third outlets are aligned and the second and fourth outlets are misaligned thereby permitting the fluid to be predominantly ejected laterally out of the device from the third outlet via the first outlet relative to the fourth outlet via the second outlet;
   wherein, in the second axial position, the first and third outlets are misaligned and the second and fourth outlets are aligned thereby permitting the fluid to be predominantly ejected laterally out of the device from the fourth outlet via the second outlet relative to the third outlet via the first outlet.

2. The device of claim 1, wherein the inner cannula is fixedly attached to the first section of the cap to prevent movement of the inner cannula during movement of the outer cannula.

3. The device of claim 1, further comprising fins that extend radially outward from the outer cannula and engage with first and second ramps of the second section.

4. The device of claim 1, wherein each of the first, second, third, and fourth outlets comprise a plurality of openings.

5. The device of claim 4, wherein:
   the plurality of openings of the first and third outlets are common in number; and
   the plurality of openings of the second and fourth outlets are common in number.

6. The device of claim 1, further comprising an opening in the distal end of each of the inner and outer cannulas.

7. A device to deliver fluid from a container to a nasal cavity, the device comprising:
   a delivery tube comprising inner and outer cannulas with the inner cannula positioned within a hollow interior of the outer cannula, each of the cannulas comprising:
   an elongated shape with a proximal end and an opposing distal end;
   a first outlet towards the distal end and positioned on a first lateral section;
   a second outlet towards the distal end and positioned on a second lateral section;
   the first outlet and second outlet of the outer cannula being exposed to an exterior of the device;
   a cap connected to both the inner cannula and the outer cannula and configured to axially position the inner and outer cannulas relative to one another between a first axial position and a second axial position;
   wherein the inner cannula is fixedly connected to the cap and the outer cannula is movable relative to the cap, the inner cannula being stationary during movement of the outer cannula;
   wherein the first axial position comprises the first outlets aligned at the first lateral section of the delivery tube and the second outlets misaligned at the second lateral section of the delivery tube to deliver the fluid out of the device in a first lateral direction;
   wherein the second axial position comprises the second outlets aligned at the second lateral section of the delivery tube and the first outlets misaligned at the first lateral section of the delivery tube to deliver the fluid out of the device in a second lateral direction.

8. The device of claim 7, wherein the proximal ends of each of the inner and outer cannulas are connected to the cap.

9. The device of claim 7, wherein one of the inner cannula and the outer cannula are threaded onto a threaded portion of the cap.

10. The device of claim 7, wherein in the first axial position the second outlets overlap a lesser amount than the first outlets such that a predominant amount of the fluid is ejected from the delivery tube in the first lateral direction and a lesser amount of the fluid is ejected from the delivery tube in the second lateral direction.

11. The device of claim 7, wherein the first outlets and the second outlets of each of the inner and outer cannulas are spaced apart around the perimeter of the cannulas by an angle of 90° or less.

12. The device of claim 7, wherein the cap comprises a plurality of members that each include an opening, the members being rotatably connected together and with the openings coaxially aligned.

* * * * *